US010160931B2

(12) United States Patent
Stork et al.

(10) Patent No.: US 10,160,931 B2
(45) Date of Patent: Dec. 25, 2018

(54) USE OF ISOMERICALLY PURE OR HIGHLY ISOMER-ENRICHED CIS- OR TRANS-(2-ISOBUTYL-4-METHYL-TETRAHYDROPYRAN-4-YL)ACETATE

(71) Applicant: BASF SE, Ludwigshafen (DE)

(72) Inventors: Timon Stork, Bürstadt Bobstadt (DE); Stefan Rüdenauer, Weinheim (DE); Margarethe Klos, Bobenheim Roxheim (DE); Ralf Pelzer, Fürstenberg (DE); Wolfgang Krause, Brühl-Rohrhof (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/514,101

(22) PCT Filed: Sep. 25, 2015

(86) PCT No.: PCT/EP2015/072083
§ 371 (c)(1),
(2) Date: Mar. 24, 2017

(87) PCT Pub. No.: WO2016/046360
PCT Pub. Date: Mar. 31, 2016

(65) Prior Publication Data
US 2017/0292084 A1 Oct. 12, 2017

(30) Foreign Application Priority Data

Sep. 26, 2014 (EP) .................. 14186627

(51) Int. Cl.
*C11B 9/00* (2006.01)
*C07D 309/10* (2006.01)
*A23L 27/20* (2016.01)

(52) U.S. Cl.
CPC .......... *C11B 9/008* (2013.01); *A23L 27/2052* (2016.08); *C07D 309/10* (2013.01)

(58) Field of Classification Search
CPC .................................... C07D 309/10
See application file for complete search history.

(56) References Cited

U.S. PATENT DOCUMENTS

| 8,618,315 | B2 | 12/2013 | Gralla et al. |
| 9,340,754 | B2 | 5/2016 | Rüdenauer et al. |
| 2013/0230476 | A1* | 9/2013 | Pelzer ............ C11B 9/008 424/70.1 |
| 2016/0060238 | A1 | 3/2016 | Stork et al. |
| 2016/0213582 | A1 | 7/2016 | Rüdenauer et al. |
| 2016/0332944 | A1 | 11/2016 | Rüdenauer et al. |
| 2017/0037020 | A1 | 2/2017 | Rüdenauer et al. |
| 2017/0037021 | A1 | 2/2017 | Stork et al. |
| 2017/0037022 | A1 | 2/2017 | Stork et al. |

FOREIGN PATENT DOCUMENTS

| EP | 0383446 A2 | 8/1990 |
| WO | WO-2010133473 A1 | 11/2010 |
| WO | WO-2011147919 A1 | 12/2011 |
| WO | WO-2011154330 A1 | 12/2011 |
| WO | WO-2016038019 A1 | 3/2016 |
| WO | WO-2016038033 A1 | 3/2016 |

OTHER PUBLICATIONS

International Search Report for PCT/EP2015/072083 dated Oct. 15, 2015.
Written Opinion of the International Searching Authority for PCT/EP2015/072083 dated Oct. 15, 2015.
U.S. Appl. No. 15/308,755, Pelzer et al.
English translation of International Preliminary Report on Patentability for PCT/EP2015/072083 dated Mar. 30, 2017.

* cited by examiner

*Primary Examiner* — John R Hardee
(74) *Attorney, Agent, or Firm* — Drinker Biddle & Reath LLP

(57) ABSTRACT

The present invention relates to the use of isomerically pure or highly isomerically enriched cis- or trans-(2-isobutyl-4-methyltetrahydropyran-4-yl) acetate for use as aroma chemicals. The invention further relates to a process for the preparation of isomerically pure or highly isomerically enriched cis- or trans-(2-isobutyl-4-methyltetrahydropyran-4-yl) acetate and the products obtainable by this process. The invention further relates to a fragrance or aroma substance composition which comprises isomerically pure or highly isomerically enriched cis- or trans-(2-isobutyl-4-methyltetra-hydropyran-4-yl) acetate, a method for imparting, and/or boosting an odor or taste of a product, and also perfumed or aromatized products which comprise isomerically pure or highly isomerically enriched cis- or trans-(2-isobutyl-4-methyltetrahydropyran-4-yl) acetate.

11 Claims, No Drawings

USE OF ISOMERICALLY PURE OR HIGHLY ISOMER-ENRICHED CIS- OR TRANS-(2-ISOBUTYL-4-METHYL-TETRAHYDROPYRAN-4-YL)ACETATE

CROSS-REFERENCE TO RELATED APPLICATIONS

This application is a national stage application (under 35 U.S.C. § 371) of PCT/EP2015/072083, filed Sep. 25, 2015, which claims benefit of European Application No. 14186627.7, filed Sep. 26, 2014, both of which are incorporated herein by reference in their entirety.

BACKGROUND OF THE INVENTION

The present invention relates to the use of isomerically pure or highly isomerically enriched cis- or trans-(2-isobutyl-4-methyltetrahydropyran-4-yl) acetate for use as aroma chemicals. The invention further relates to a method for the preparation of isomerically pure or highly isomerically enriched cis- or trans-(2-isobutyl-4-methyltetrahydropyran-4-yl) acetate and the products obtainable by this process. The invention furthermore relates to a fragrance or flavor composition which comprises isomerically pure or highly isomerically enriched cis- or trans-(2-isobutyl-4-methyltetrahydropyran-4-yl) acetate, to a method for imparting and/or intensifying an odor or flavor of a product, and also perfumed or flavored products which comprise isomerically pure or highly isomerically enriched cis- or trans-(2-isobutyl-4-methyltetrahydropyran-4-yl) acetate.

PRIOR ART

Despite a large number of existing aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should, however, also have additional positive secondary properties, such as e.g. an efficient preparation method, the possibility of providing better sensory profiles as a result of synergistic effects with other fragrances, a higher stability under certain application conditions, a higher extendability, a better staying power, etc.

2-Substituted 4-hydroxy-4-methyltetrahydropyrans are known valuable compounds for use as aroma chemicals. Thus, for example, the cis/trans-diastereomer mixture of 2-(2-methylpropyl)-4-hydroxy-4-methyltetrahydropyran

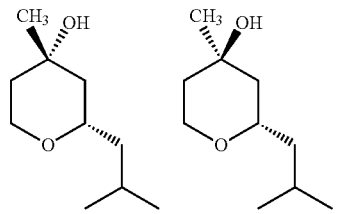

is distinguished by a pleasant lily of the valley scent and is suitable to a particular extent for use as aroma chemical, e.g. for producing fragrance compositions. It would be desirable if further aroma chemicals could be produced by simple derivatization of these 2-substituted 4-hydroxy-4-methyltetrahydropyrans such that new, cost-effective consecutive products result. Also desirable would be compounds which, in combination with 2-substituted 4-hydroxy-4-methyltetrahydropyrans, have an advantageous sensory profile.

EP 0383446 A2 describes the synthesis and the olfactory properties of a large number of different 2,4,4-trisubstituted tetrahydropyranyl esters. Example IX describes the synthesis of 2-isobutyl-4-methyltetrahydropyran-4-yl acetate by esterification of 2-isobutyl-4-hydroxy-4-methyltetrahydropyran with acetic anhydride in the presence of methanesulfonic acid. Although the reaction product was subjected to fractional distillation, the resulting fractions were not analyzed either with regard to the components present therein nor as regards their olfactory properties. The depicted NMR spectrum (FIG. 17) suggests a cis/trans ratio in the range from 75:25 to 80:20. For the combined fractions 11 to 17, a sandalwood-like, floral, rose-like odor profile is stated. This document comprises no reference to the preparation and properties of isomerically pure or highly isomerically enriched cis- or trans-(2-isobutyl-4-methyltetrahydropyran-4-yl) acetate.

The object of the present invention is to provide new aroma chemicals with advantageous properties. These should specifically have pleasant odiferous properties. Furthermore, they should be capable, in combination with other aroma chemicals, of providing novel advantageous sensory profiles. Moreover, they should be able to be prepared and/or isolated effectively.

Surprisingly, it has now been found that this object is achieved by isomerically pure or highly isomerically enriched cis- or trans-(2-isobutyl-4-methyltetrahydropyran-4-yl) acetate and its use as aroma chemical.

SUMMARY OF THE INVENTION

The invention provides the use of isomerically pure cis-(2-isobutyl-4-methyltetrahydropyran-4-yl) acetate of the formula (I.1) or of isomerically pure trans-(2-isobutyl-4-methyltetrahydropyran-4-yl) acetate of the formula (I.2) or of an isomer mixture of cis-2-isobutyl-4-methyltetrahydropyran-4-yl) acetate (I.1) and trans-(2-isobutyl-4-methyltetrahydropyran-4-yl) acetate (I.2)

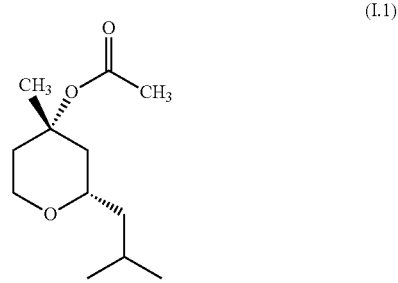

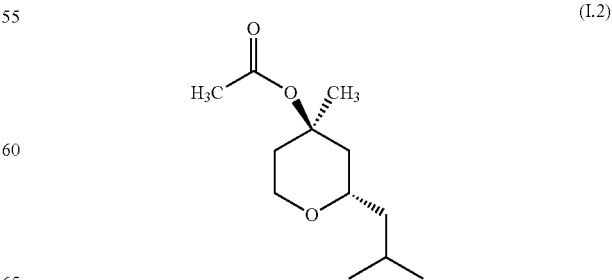

wherein, when using an isomer mixture, the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight, or the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight, as aroma chemical.

The invention further provides a process for the preparation of isomerically pure cis-(2-isobutyl-4-methyltetrahydropyran-4-yl) acetate of the formula (I.1) or of isomerically pure trans-(2-isobutyl-4-methyltetrahydropyran-4-yl) acetate of the formula (I.2) or of an isomer mixture of (I.1) and (I.2), where the weight fraction of (I.1) or the weight fraction of (I.2) in the isomer mixture, based on the total weight of (I.1) and (I.2), is in a range from 90% by weight to less than 100% by weight, in which
i) an isomer mixture of cis-2-(2-methylpropyl)-4-hydroxy-4-methyltetrahydropyran (II.1) and trans-2-(2-methylpropyl)-4-hydroxy-4-methyltetrahydropyran (II2)

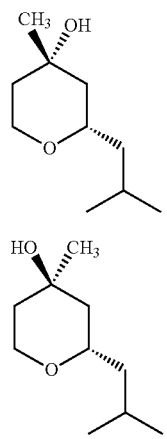

is reacted with a compound of the formula CH$_3$C(=O)—X, in which X is Cl, Br or CH$_3$C(=O)O, ii) optionally the reaction mixture obtained in step i) is subjected to a separation to give at least one fraction which comprises isomerically pure (I.1) or isomerically pure (I.2) or an isomer mixture of (I.1) and (I.2), where the weight fraction of (I.1) or the weight fraction of (I.2) in the isomer mixture, based on the total weight of (I.1) and (I.2), is in a range from 90% by weight to less than 100% by weight.

The invention further provides isomerically pure cis-(2-isobutyl-4-methyltetrahydropyran-4-yl) acetate of the formula (I.1).

The invention further provides an isomer mixture of cis-(2-isobutyl-4-methyltetrahydropyran-4-yl) acetate (I.1) and trans-(2-isobutyl-4-methyltetrahydropyran-4-yl) acetate (I.2), in which the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight.

The invention further provides isomerically pure trans-(2-isobutyl-4-methyltetrahydropyran-4-yl) acetate of the formula (I.2).

The invention further provides an isomer mixture of cis-(2-isobutyl-4-methyltetrahydropyran-4-yl) acetate (I.1) and trans-(2-isobutyl-4-methyltetrahydropyran-4-yl) acetate (I.2), in which the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight.

The invention further provides a fragrance or flavor composition comprising
a) isomerically pure cis-(2-isobutyl-4-methyltetrahydropyran-4-yl) acetate of the formula (I.1) or isomerically pure trans-(2-isobutyl-4-methyltetrahydropyran-4-yl) acetate of the formula (I.2) or an isomer mixture of cis-(2-isobutyl-4-methyltetrahydropyran-4-yl) acetate (I.1) and trans-(2-isobutyl-4-methyltetrahydropyran-4-yl) acetate (I.2), where the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight, or the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight,
b) optionally at least one further aroma chemical different from the compounds (I.1) and (I.2), and
c) optionally at least one diluent,
with the proviso that the composition comprises at least one component b) or c).

The invention further provides a method for imparting and/or replacing and/or intensifying an odor or flavor of a product with a fresh-floral note, in particular an iris-like note, a citrus note, in particular a bergamot-like note, such as e.g. the note of linalyl acetate or ethyllinalyl acetate, a woody note or a pepper/nutmeg-like note, in which the product is brought into contact with an organoleptically effective amount of an isomerically pure cis-(2-isobutyl-4-methyltetrahydropyran-4-yl) acetate of the formula (I.1) or an isomer mixture, where the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight.

The invention further provides a method for imparting and/or intensifying an odor or flavor of a product with a jasmine-like note, a leather-like note or a strong fruit-like note, in which the product is brought into contact with an organoleptically effective amount of an isomerically pure trans-(2-isobutyl-4-methyltetrahydropyran-4-yl) acetate of the formula (I.2) or an isomer mixture, where the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight.

The invention further provides a perfumed or flavored product, comprising an organoleptically effective amount of isomerically pure cis-(2-isobutyl-4-methyltetrahydropyran-4-yl) acetate of the formula (I.1) or of isomerically pure trans-(2-isobutyl-4-methyltetrahydropyran-4-yl) acetate of the formula (I.2) or highly isomerically enriched (I.1) or highly isomerically enriched (I.2), or comprising an organoleptically effective amount of a fragrance or flavor composition according to the invention as defined above and below.

The invention further provides the use of isomerically pure cis-(2-isobutyl-4-methyltetrahydropyran-4-yl) acetate of the formula (I.1) or of an isomer mixture, where the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight, for the partial or complete replacement of linalyl acetate in a fragrance or flavor composition comprising linalyl acetate or in a product flavored or perfumed with linalyl acetate.

DESCRIPTION OF THE INVENTION

The invention has the following advantages:

With isomerically pure or highly isomerically enriched cis- or trans-(2-isobutyl-4-methyltetrahydropyran-4-yl) acetate, new compounds are provided for use as aroma chemical and specifically as fragrance which provide very advantageous olfactory properties. Isomerically pure cis-(2-isobutyl-4-methyltetrahydropyran-4-yl) acetate of the formula (I.1) and isomer mixtures with a weight fraction of cis-(2-isobutyl-4-methyltetrahydropyran-4-yl) acetate of at least 90% by weight are suitable for producing scents with floral and citrus-like notes, such as e.g. an iris-like note, a bergamot-like note, a linalyl acetate-like note (linalyl acetate is one of the main components in lavender oil and bergamot oil), a woody note or a pepper/nutmeg note Isomerically pure trans-(2-isobutyl-4-methyltetrahydropyran-4-yl) acetate of the formula (I.2) and isomer mixtures with a weight fraction of trans-(2-isobutyl-4-methyltetrahydropyran-4-yl) acetate of at least 90% by weight are suitable for producing scents with a jasmine-like note, a leather-like note or a strong fruit-like note. These odor properties differ significantly from those which are attributed to the mixture according to EP 0383446.

Isomerically pure or highly isomerically enriched cis- or trans-(2-isobutyl-4-methyltetrahydropyran-4-yl) acetate permits the provision of facet-rich sensory profiles as a result of synergistic effects with other odorants. Thus, e.g. in the combination of isomerically pure or highly isomerically enriched cis-(2-isobutyl-4-methyltetrahydropyran-4-yl) acetate with 2-substituted 4-hydroxy-4-methyltetrahydropyrans, odor profiles are attained which are suitable for floral compositions with bergamot and fruit character. For the combination of isomerically pure or highly isomerically enriched cis-(2-isobutyl-4-methyltetrahydropyran-4-yl) acetate with linalyl acetate, odor profiles are attained which are likewise very facet-rich.

The preparation of isomerically pure or highly isomerically enriched cis- or trans-(2-isobutyl-4-methyltetrahydropyran-4-yl) acetate can be easily integrated into the preparation of 2-isobutyl-4-hydroxy-4-methyltetrahydropyran. The preparation is performed for example starting from 2-isobutyl-4-hydroxy-4-methyltetrahydropyran by esterification and subsequent fractional distillation of the esterification product.

Unless stated more precisely below, the terms
cis-(2-isobutyl-4-methyltetrahydropyran-4-yl) acetate (I.1) and trans-(2-isobutyl-4-methyltetrahydropyran-4-yl) acetate (I.2)
refer to all enantiomers in pure form, optically active mixtures of the enantiomers of these compounds, and also optically inactive racemates of cis-(I.1) and trans-(I.2). Wherever the discussion below is of cis- and trans-diastereomers of the compounds (I.1) or (I.2), only one of the enantiomeric forms is depicted in each case. The isomers of 2-isobutyl-4-methyltetrahydropyran-4-yl) acetate are reproduced below merely for the purposes of illustration:

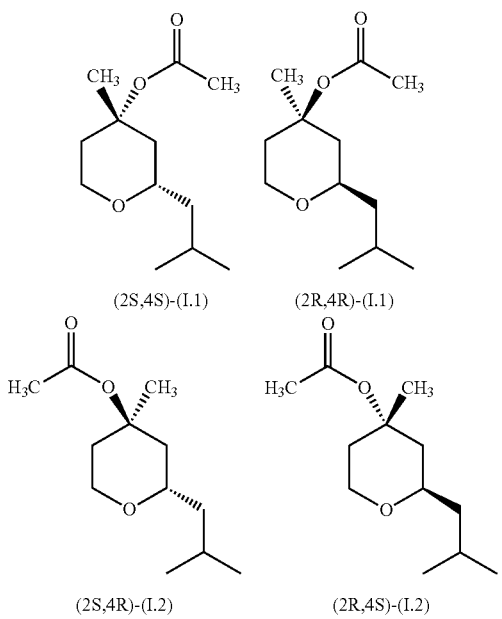

The compound of the formula (I.1) can be used in stereoisomerically pure form or as (2S,4S)- and (2R,4R)-isomer mixture.

The compound of the formula (I.2) can be used in stereoisometrically pure form or as (2S,4R)- and (2R,4S)-isomer mixture.

In a specific embodiment, optically inactive racemates are used in accordance with the invention.

Hereinbelow, an isomer mixture of cis-(2-isobutyl-4-methyltetrahydropyran-4-yl) acetate (I.1) and trans-(2-isobutyl-4-methyltetrahydropyran-4-yl) acetate (I.2), where the weight fraction of cis-(2-isobutyl-4-methyltetrahydropyran-4-yl) acetate (I.1), based on the total weight of cis-2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight, is referred to as "highly isomerically enriched cis-(2-isobutyl-4-methyltetrahydropyran-4-yl) acetate" or as "highly isomerically enriched (I.1)".

Hereinbelow, isomerically pure cis-(2-isobutyl-4-methyltetrahydropyran-4-yl) acetate (I.1) is the term used to refer to the pure cis isomer. An isomerically pure cis-(2-isobutyl-4-methyltetrahydropyran-4-yl) acetate (I.1) comprises no (i.e. 0% by weight) trans-(2-isobutyl-4-methyltetrahydropyran-4-yl) acetate (I.2). The term "isomerically pure" in this context refers only to the cis/trans isomerism and not to the enantiomerism.

Hereinbelow, an isomer mixture of cis-(2-isobutyl-4-methyltetrahydropyran-4-yl) acetate (I.1) and trans-(2-isobutyl-4-methyltetrahydropyran-4-yl) acetate (I.2), where the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl)acetate (I.2), is in a range from 90% by weight to less than 100% by weight, is referred to as "highly isomerically enriched trans-(2-isobutyl-4-methyltetrahydropyran-4-yl) acetate" or as "highly isomerically enriched (I.2)".

Hereinbelow, isomerically pure trans-(2-isobutyl-4-methyltetrahydropyran-4-yl) acetate (I.2) is the term used to refer to the pure trans isomer. An isomerically pure trans-(2-isobutyl-4-methyltetrahydropyran-4-yl) acetate (I.2) comprises no (i.e. 0% by weight) cis-(2-isobutyl-4-methyltetrahydropyran-4-yl) acetate (I.1). The term "isomerically pure" in this context refers only to the cis/trans isomerism and not to the enantiomerism.

Preferably, highly isomerically enriched (I.1) has a weight fraction of cis-(2-isobutyl-4-methyltetrahydropyran-4-yl) acetate (I.1), based on the total weight of cis-2-isobutyl-4-methyltetrahydropyran-4-yl) acetate (I.1) and trans-(2-isobutyl-4-methyltetrahydropyran-4-yl) acetate (I.2), of from 90 to 99.999% by weight, particularly preferably from 92 to 99.99% by weight, in particular from 95 to 99.9% by weight.

Preferably, highly isomerically enriched (I.2) has a weight fraction of trans-(2-isobutyl-4-methyltetrahydropyran-4-yl) acetate (I.2), based on the total weight of cis-2-isobutyl-4-methyltetrahydropyran-4-yl) acetate (I.1) and trans-(2-isobutyl-4-methyltetrahydropyran-4-yl) acetate (I.2) of from 90 to 99.999% by weight, particularly preferably of from 92 to 99.99% by weight, in particular from 95 to 99.9% by weight.

In the context of the present invention, an organoleptically effective amount is to be understood as meaning an amount which suffices, upon application as intended, to bring about a scent impression for the user or consumer. When using isomerically pure or highly isomerically enriched (I.1), this is specifically the impression of a pleasant odor of iris, bergamot oil or linalyl acetate. When using isomerically pure or highly isomerically enriched (I.2), it is specifically the impression of a pleasant odor of jasmine.

Preparation of isomerically pure or highly isomerically enriched (2-Isobutyl-4-methyltetrahydropyran-4-yl) acetate The preparation of isomerically pure or isomerically enriched (2-isobutyl-4-methyltetrahydropyran-4-yl) acetate preferably comprises an esterification of a 2-isopropyl-4-hydroxy-4-methyltetrahydropyran of the general formula (II). Converting 2-isopropyl-4-hydroxy-4-methyltetrahydropyran (II) to the corresponding acetates of the general formula (I) can take place by customary processes known to the person skilled in the art in accordance with the following scheme.

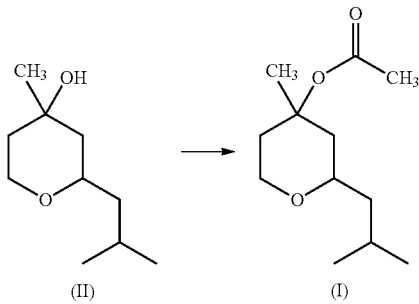

During the esterification reaction, the configuration of the alcohol component (II) used generally does not change. To prepare isomerically pure or isomerically enriched (2-isobutyl-4-methyltetrahydropyran-4-yl) acetate, in a first embodiment it is thus possible to start from an isomerically pure alcohol component (II) or an alcohol component (II) which is already sufficiently highly enriched in the desired isomer. In a second embodiment, an isomer mixture is used for the esterification which is still not sufficiently highly enriched in the desired isomer, and then a fraction sufficiently enriched in the desired isomer is isolated from the product of the esterification.

The invention therefore further provides a process for the preparation of isomerically pure (I.1) or of isomerically pure (I.2) or of highly isomerically enriched (I.1) or of highly isomerically enriched (I.2), in which i) an isomer mixture of cis-2-(2-methylpropyl)-4-hydroxy-4-methyltetrahydropyran (II.1) and trans-2-(2-methylpropyl)-4-hydroxy-4-methyltetrahydropyran (II.2) is reacted with a compound of the formula $CH_3C(=O)-X$, in which X is Cl, Br or $CH_3C(=O)O$, ii) optionally the reaction mixture obtained in step i) is subjected to a separation to give at least one fraction which comprises isomerically pure (I.1) or isomerically pure (I.2) or highly isomerically enriched (I.1) or highly isomerically enriched (I.2), Processes for the preparation of 2-isopropyl-4-hydroxy-4-methyltetrahydropyran (II), e.g. by reaction of isoprenol with prenal and subsequent hydrogenation, are known to the person skilled in the art. Suitable processes are described e.g. in WO 2011/147919, WO 2011/154330 and WO 2010/133473, to which reference is made here in its entirety.

For the esterification, 2-isopropyl-4-hydroxy-4-methyltetrahydropyran of the general formula (II) can be reacted with acetic acid or a suitable derivative thereof. Suitable derivatives are e.g. the acid halides and acid anhydrides. I.e. the compound (II) is reacted with a compound of the formula $CH_3C(=O)-X$, in which X is Cl, Br or $CH_3C(=O)O$.

The esterification preferably takes place in the presence of an esterification catalyst. Esterification catalysts that can be used are the catalysts customary for this purpose, e.g. mineral acids, such as sulfuric acid and phosphoric acid; organic sulfonic acids, such as methanesulfonic acid and p-toluenesulfonic acid; amphoteric catalysts, in particular titanium, tin(IV) or zirconium compounds, such as tetraalkoxytitaniums, e.g. tetrabutoxytitanium, and tin(IV) oxide. The esterification catalyst is used in an effective amount, which is usually in the range from 0.05 to 10% by weight, preferably 0.1 to 5% by weight, based on the sum of acid component (or anhydride) and alcohol component.

The esterification can generally take place at ambient pressure or reduced or increased pressure. Preferably, the esterification is carried out at ambient pressure or reduced pressure.

The esterification can be carried out in the absence of an added solvent or in the presence of an organic solvent. If the esterification is carried out in the presence of a solvent, it is preferably an organic solvent that is inert under the reaction conditions. These include, for example, aliphatic hydrocarbons, halogenated aliphatic hydro-carbons, aromatic and substituted aromatic hydrocarbons or ethers. Preferably, the solvent is selected from pentane, hexane, heptane, ligroin, petroleum ether, cyclo-hexane, dichloromethane, trichloromethane, tetrachloromethane, benzene, toluene, xylene, chlorobenzene, dichlorobenzenes, dibutyl ether, THF, dioxane and mixtures thereof.

The esterification is usually carried out in a temperature range from 0 to 200° C., preferably 10 to 150° C.

The esterification can take place in the absence or the presence of an inert gas. As a rule, an inert gas is understood as meaning a gas which, under the stated reaction conditions, does not enter into any reactions with the starting materials, reagents or solvents involved in the reaction or the resulting products. These include e.g. nitrogen or argon.

In a specific embodiment, to prepare an isomerically pure cis-(2-isobutyl-4-methyltetrahydropyran-4-yl) acetate of the formula (I.1) or an isomerically pure trans-(2-isobutyl-4-methyltetrahydropyran-4-yl) acetate of the formula (I.2) or a highly isomerically enriched (I.1) or a highly isomerically enriched (I.2), a reaction mixture of the 2-isobutyl-4-methyltetrahydropyran-4-yl) acetate synthesis is subjected to a separation to give a fraction which isolates isomerically pure cis-(I.1) or isomerically pure trans-(I.2) or a fraction enriched in the cis isomer or in the trans isomer.

The customary aforementioned processes for the preparation of 2-isobutyl-4-methyltetrahydropyran-4-yl) acetate lead to reaction products with a cis/trans ratio in the range from about 80:20 to 20:80. Accordingly, the reaction mixture of the (2-isobutyl-4-methyltetrahydropyran-4-yl) acetate synthesis usually also has a cis/trans ratio in the range from about 80:20 to 20:80. To prepare 2-isobutyl-4-methyltetrahydropyran-4-yl acetate, it is of course possible in principle to use a 2-isopropyl-4-hydroxy-4-methyl-tetrahydropyran with any desired cis/trans ratio. These may be, for example, technically available streams from the synthesis of the 2-isopropyl-4-hydroxy-4-methyltetrahydropyran or their work-up.

Preferably, the isolation of a fraction which comprises isomerically pure (I.1) or isomerically pure (I.2) or highly isomerically enriched (I.1) or highly isomerically enriched (I.2) (=step ii)) takes place by means of fractional distillation.

Suitable devices for distillative separation comprise distillation columns, such as tray columns, which can be equipped with bubble caps, sieve plates, sieve trays, arranged packings, dumped packings, valves, side take-offs, etc., evaporators, such as thin-film evaporators, falling film evaporators, forced circulation evaporators, Sambay evaporators, etc., and combinations thereof.

The distillation columns can have separation-effective internals, which are preferably selected from separation trays, arranged packings, e.g. sheet-metal or fabric packings, such as Sulzer Mellapak®, Sulzer BX, Montz B1 or Montz A3 or Kühni Rombopak, or irregular beds of dumped packings, such as e.g. Dixon rings, Raschig rings, high-flow rings or Raschig super rings. Arranged packings, preferably sheet-metal or fabric packings, with a specific surface area of from 100 to 750 $m^2/m^3$, in particular 250 to 500 $m^2/m^3$, have proven particularly useful. They permit high separation efficiencies coupled with low pressure losses.

Use of isomerically pure or highly isomerically enriched cis- or trans-(2-isobutyl-4-methyltetrahydropyran-4-yl) acetate The process described above allows the provision of isomerically pure or highly isomerically enriched cis- or trans-(2-isobutyl-4-methyltetrahydropyran-4-yl) acetate.

The (cis-(2-isobutyl-4-methyltetrahydropyran-4-yl) acetate of the formula (I.1)) used) according to the invention has a weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2) of from 90 to 100% by weight, preferably from 90 to 99.999% by weight, particularly preferably from 92 to 99.99% by weight, in particular from 95 to 99.9% by weight.

The (trans-(2-isobutyl-4-methyltetrahydropyran-4-yl) acetate of the formula (I.2)) used) according to the invention has a weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) of from 90 to 100% by weight, preferably from 90 to 99.999% by weight, particularly from 92 to 99.99% by weight, in particular from 95 to 99.9% by weight.

A preferred embodiment is the use of isomerically pure or highly isomerically enriched (I.1) for producing a scent with an iris-like note, a bergamot-like note, a linalyl acetate-like note, a woody note or a pepper/nutmeg-like note.

A further preferred embodiment is the use of isomerically pure or highly isomerically enriched (I.2) for producing a scent with a jasmine-like note, a leather-like note or a strong fruit-like note.

A further preferred embodiment is the use of isomerically pure or highly isomerically enriched (I.1) for the partial or complete replacement of linalyl acetate in a fragrance or flavor composition comprising linalyl acetate or in a product flavored or perfumed with linalyl acetate.

Further Aroma Chemicals:

The isomerically pure or highly isomerically enriched cis- or trans-(2-isobutyl-4-methyltetrahydropyran-4-yl) acetate according to the invention or used according to the invention is used, in a preferred embodiment of the invention, in combination with at least one further aroma chemical different from the compounds (I.1) and (I.2). Preferably, the aroma chemicals different from the compounds (I.1) and (I.2) are odorants. Odorant composition according to the invention then comprise for example 1, 2, 3, 4, 5, 6, 7, 8 or more further odorants.

Further flavors and specifically odorants can be found e.g. in S. Arctander, Perfume and Flavor Chemicals, Vol. I and II, Montclair, N.J., 1969, self published or K. Bauer, D. Garbe and H. Surburg, Common Fragrance and Flavor Materials, $4^{th}$. Ed., Wiley-VCH, Weinheim 2001.

Specifically, mention may be made of:

extracts from natural raw materials such as essential oils, concretes, absolutes, resins, resinoids, balsams, tinctures such as e.g. ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; ylang ylang oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E,Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclo-pentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopenta-decenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9-cyclo-heptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethyl-phenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacet-aldehyde; 3-phenylpropanal; hydratropaaldehyde; 4-methylbenzaldehyde; 4-methyl-phenylacetaldehyde; 3-(4-ethylphenyl)-2,2-dimethylpropanal; 2-methyl-3-(4-isopropyl-phenyl)propanal; 2-methyl-3-(4-tert-butylphenyl)propanal; 2-methyl-3-(4-isobutylphenyl) propanal; 3-(4-tert-butylphenyl)propanal; cinnamaldehyde; alpha-butylcinnanialdehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxy-benzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzo-furanylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl) propanal or 2,4-dimethyl-3-cyclohexenecarbaldehyde; 6-isopropylquinoline; 6-isobutylquinoline; 6-sec-butyl-quinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The further aroma chemical different from the compounds (I.1) and (I.2) is preferably selected from 2-isobutyl-4-methyltetrahydro-2H-pyran-4-ol, linalyl acetate, 7-hydroxy-3,7-dimethyloctanal, 4-isopropylcyclohexylmethanol, 4-(octahydro-4,7-methano-5H-inden-5-ylidene)butanal, 4-(4-hydroxy-4-methylpentyl)-3-cyclohexene-1-carboxaldehyde, 3-(4-hydroxy-4-methylpentyl)-3-cyclohexene-1-carboxaldehyde, 2,5,7,7-tetramethyloctanal, 2-methyl-3-(4-tert-butylphenyl)propanal, 3-(4-tert-butylphenyl) propanal, linalool, ethyllinalool, tetrahydrolinalool and 2-methyl-4-phenyl-2-butanol).

Fragrance or Flavor Composition

The invention further provides a fragrance or flavor composition comprising a) isomerically pure cis-(2-isobutyl-4-methyltetrahydropyran-4-yl) acetate of the formula (I.1) or isomerically pure trans-(2-isobutyl-4-methyltetrahydropyran-4-yl) acetate of the formula (I.2) or an isomer mixture of cis-(2-isobutyl-4-methyltetrahydropyran-4-yl) acetate (I.1) and trans-(2-isobutyl-4-methyltetrahydropyran-4-yl) acetate (I.2), where the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight, or the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight, b) optionally at least one further aroma chemical different from the compounds (I.1) and (I.2), and c) optionally at least one diluent, with the proviso that the composition comprises at least one component b) or c).

Preferably, the fragrance or flavor composition according to the invention comprises the component a) in a weight fraction of from 0.1 to 95% by weight, particularly preferably from 0.1 to 90% by weight, in particular from 0.1 to 80% by weight, based on the total weight of the composition.

More preferably, the fragrance or flavor composition according to the invention comprises the component a) in a weight fraction of from 0.1 to 70% by weight, more preferably 1 to 50% by weight, based on the total weight of the composition. In a specific embodiment, the fragrance or flavor composition according to the invention comprises the component a) in a weight fraction of from 2 to 30% by weight, more specifically 3 to 15% by weight, based on the total weight of the composition.

In a preferred embodiment, the fragrance or flavor composition according to the invention comprises the component a) as the sole aroma chemical.

In a further preferred embodiment, the fragrance or flavor composition according to the invention comprises at least one further aroma chemical b) different from the compounds (I.1) and (I.2).

Suitable further aroma chemicals b) are those mentioned above, to which reference is made here in their entirety.

Preferably, the quantitative weight ratio of component a) to component b) is in a range from 100:1 to 1:100, particularly preferably from 50:1 to 1:50.

The fragrance or flavor composition can optionally comprise at least one diluent c). Suitable diluents can be used individually or as a mixture of 2 or more than 2 diluents. Suitable diluents are those as are customarily used as solvents for fragrances or flavors.

Preferably, the fragrance or flavor composition comprises, as diluents c), at least one compound which is liquid at 20° C. and 1013 mbar.

Preferably, the compounds of component a) have a solubility in component c) at 20° C. of at least 0.1 mg/ml, particularly preferably of at least 0.5 mg/ml. Preferably, if present, the compounds of component b) have a solubility in component c) at 20° C. of at least 0.1 mg/ml, particularly preferably of at least 0.5 mg/ml.

Component c) is preferably selected from aliphatic and cycloaliphatic monoalcohols, polyols, open-chain aliphatic ethers, cyclic ethers, polyol mono- and polyethers, esters and mixtures thereof.

Suitable aliphatic and cycloaliphatic monoalcohols are e.g. ethanol, n-propanol, isopropanol, n-butanol, sec-butanol, tert-butanol and cyclohexanol.

Suitable polyols are ethylene glycol, propylene glycol, 1,2-butylene glycol, diethylene glycol, dipropylene glycol or glycerol.

Suitable open-chain aliphatic ethers and cyclic ethers are e.g. diethyl ether, dipropyl ether, diisopropyl ether, methyl tert-butyl ether, tetrahydrofuran, tetrahydropyran, 1,4-dioxane or morpholine.

Suitable polyol mono- and polyethers are e.g. ethylene glycol monomethyl ether, ethylene glycol dimethyl ether, ethylene glycol monoethyl ether, ethylene glycol diethyl ether, propylene glycol monoethyl ether, propylene glycol diethyl ether or diethylene glycol monoethyl ether.

Suitable esters are ethyl acetate, methyl acetate, propyl acetate, isopropyl acetate, n-butyl acetate, sec-butyl acetate, tert-butyl acetate, isobutyl acetate, isoamyl acetate, ethyl butyrates, ethyl lactate, diethyl carbonate, ethylene carbonates, propylene carbonate, triethyl citrate, isopropyl myristate, diethyl phthalate, dialkyl esters of 1,2-cyclohexanedicarboxylic acid, specifically 1,2-cyclohexanedicarboxylic acid diisononyl ester (Hexamoll® DINCH, BASF SE), etc.

Perfumed or Flavored Product

Isomerically pure or highly isomerically enriched cis- or trans-(2-isobutyl-4-methyltetrahydropyran-4-yl) acetate according to the invention and used according to the invention can be incorporated into a series of products and/or be applied to such products.

Odorants according to the invention can be used in the production of perfumed articles. The olfactory properties, like the material properties (such as solubility in customary solvents and compatibility with further customary constituents of such products), as well as the toxicological acceptability of the odorants according to the invention underline their particular suitability for the stated use purposes. The positive properties contribute to the fact that the odorants used according to the invention and the odorant compositions according to the invention are particularly preferably used in perfume products, body care products, hygiene articles, textile detergents, and in cleaners for solid surfaces.

The perfumed article is e.g. selected from perfume products, body care products, hygiene articles, textile detergents and cleaners for solid surfaces. Preferred perfumed articles according to the invention are also selected from among:

perfume products selected from perfume extracts, Eau de Parfums, Eau de Toilettes, Eau de Colognes, Eau de Solide, Extrait Parfum, air fresheners in liquid form, gel-like form or a form applied to a solid carrier, aerosol sprays, scented cleaners and oils;

body care products selected from aftershaves, pre-shave products, splash colognes, solid and liquid soaps, shower gels, shampoos, shaving soaps, saving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, hair shampoo, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics such as e.g. eyeshadows, nail varnishes, make-ups, lipsticks, mascara, toothpaste, dental floss;

hygiene articles selected from candles, lamp oils, joss sticks, insecticides, repellents, propellants, rust removers, perfumed freshening wipes, armpit pads, baby diapers, sanitary towels, toilet paper, cosmetic wipes, pocket tissues, dishwasher deodorizer;

cleaners for solid surfaces selected from perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners;

textile detergents selected from liquid detergents, powder detergents, laundry pretreatments such as bleaches, soaking agents and stain removers, fabric softeners, washing soaps, washing tablets.

According to a further aspect, the odorants used according to the invention and the odorant compositions according to the invention are suitable for use in surfactant-containing perfumed articles. This is because odorants and/or odorant compositions with a musk note and pronounced naturalness are often sought—especially for the perfuming of surfactant-containing formulations such as, e.g., cleaners (in particular dishwashing detergents and all-purpose cleaners).

According to a further aspect, odorants used according to the invention and odorant compositions according to the invention can be used as agents for providing (a) hair or (b) textile fibers with a rosy odor note.

The odorants to be used according to the invention and odorant compositions according to the invention are therefore particularly well suited for use in surfactant-containing perfumed articles.

It is preferred if the perfumed article is one of the following:

an acidic, alkaline or neutral cleaner which is selected in particular from the group consisting of all-purpose cleaners, floor cleaners, window cleaners, dishwashing detergents, bath and sanitary cleaners, scouring milk, solid and liquid toilet cleaners, powder and foam carpet cleaners, liquid detergents, powder detergents, laundry pretreatments such as bleaches, soaking agents and stain removers, fabric softeners, washing soaps, washing tablets, disinfectants, surface disinfectants, an air freshener in liquid form, gel-like form or a form applied to a solid carrier or as an aerosol spray, a wax or a polish, which is selected in particular from the group consisting of furniture polishes, floor waxes and shoe creams, or a body care composition, which is selected in particular from the group consisting of shower gels and shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics.

Ingredients with which odorants used according to the invention or odorant compositions according to the invention can preferably be combined are, for example: preservatives, abrasives, antiacne agents, agents to combat skin aging, antibacterial agents, anticellulite agents, antidandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emollients, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, detergents, fabric softeners, suspending agents, skin-tanning agents, thickeners, vitamins, oils, waxes, fats, phospholipids, saturated fatty acids, mono- or polyunsaturated fatty acids, a-hydroxy acids, polyhydroxy fatty acids, liquefiers, dyes, color-protection agents, pigments, anticorrosives, aromas, flavorings, odorants, polyols, surfactants, electrolytes, organic solvents or silicone derivatives.

According to a further aspect, the odorants are used in the production of the perfumed articles in liquid form, undiluted or diluted with a solvent or in the form of an odorant composition. Suitable solvents for this purpose are those mentioned above as component c). Reference is made hereto in their entirety.

The odorants and/or odorant compositions present in the perfumed articles according to the invention can in this connection, in one embodiment, be absorbed onto a carrier, which ensures both fine distribution of the odorant or odorant composition within the product and controlled release upon use. Carriers of this type may be porous inorganic materials such as light sulfate, silica gels, zeolites, gypsums, clays, clay granules, aerated concrete, etc. or organic materials such as woods and cellulose-based materials, The odorants used according to the invention and the odorant compositions according to the invention can also be in microencapsulated form, spray-dried form, in the form of inclusion complexes or in the form of extrusion products and be added in this form to the product or article to be perfumed. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the perfume oil, wherein carrier substances that can be used are modified starches, proteins, dextrin and vegetable gums. Inclusion complexes can be prepared e.g. by introducing dispersions of odorant compositions and cyclodextrins or urea derivatives into a suitable solvent, e.g. water. Extrusion products can be produced by melting odorants used according to the invention and odorant compositions according to the invention with a suitable wax-like substance and by extrusion with subsequent solidification, optionally in a suitable solvent, e.g. isopropanol.

The examples below serve to illustrate the invention without limiting it in any way.

EXAMPLES

Synthesis:

The esterification of an isomer mixture of cis-2-(2-methylpropyl)-4-hydroxy-4-methyltetrahydropyran (II.1) and trans-2-(2-methylpropyl)-4-hydroxy-4-methyltetrahydropyran (II.2) was performed by reaction with acetic anhydride and catalytic amounts of methanesulfonic acid by a process known to the person skilled in the art. Such a process is described in EP 0383446 A2.

Distillation:

In a laboratory batch column, 1.4 kg of crude product from the pyranol acetate synthesis, comprising approx. 71 GC area % cis-pyranol acetate (area % values ascertained by means of gas chromatography), approx. 19 GC area % trans-pyranol acetate, approx. 6 GC area % residual solvent and approx. 4 GC area % unreacted 2-(2-methylpropyl)-4-hydroxy-4-methyltetrahydropyran, were distilled. The laboratory batch column used consisted of a 1.6 L distillation boiler which is electrically heatable. Attached to the boiler is a 43 mm-wide rectification section with 1.4 m packing (Montz A3-1000) made of glass, which corresponds to approximately 20 theoretical plates. On the column there is a condenser which was operated at 15° C. The condensate was divided upon flowing down onto the column by a reflux divider into a reflux stream and a distillate stream.

The fractionation was carried out at a top pressure of 4 mbar and a constant reflux ratio of 10:1. In the process, 13 fractions (see diagram 1) were obtained. The top temperature during the overall distillation was in the range from 83 to 92° C. In diagram 1, RT stands for retention time in minutes.

Diagram 1: Composition of the fractions in GC area % of the distillation of pyranol acetate

| GC analysis | Division g | % | Σ % | Toluene RT 4.9 | trans-pyranol acetate RT 23.3 | cis-pyranol acetate RT 26.9 | Total pyranol acetate | Pyranol trans RT 27.1 | Pyranol cis RT 28.5 | Remainder |
|---|---|---|---|---|---|---|---|---|---|---|
| | | | | | | Areas % | | | | |
| Feed | 1417 | 100.00 | 0.00 | 6.26 | 18.49 | 71.22 | 89.71 | 1.90 | 1.83 | 0.30 |
| Cool trap | 70 | 4.94 | 4.94 | 94.35 | 0.69 | 0.02 | 0.71 | 0.05 | 0.02 | 4.87 |
| Fraction 1 | 88 | 6.21 | 11.15 | 0 | 89.8 | 0.08 | 89.88 | 9.04 | 0.40 | 0.68 |
| Fraction 2 | 94 | 6.63 | 17.78 | 0 | 88.39 | 0.02 | 88.41 | 8.85 | 2.52 | 0.22 |
| Fraction 3 | 58 | 4.09 | 21.88 | 0 | 78.8 | 2.12 | 80.92 | 9.07 | 9.58 | 0.43 |
| Fraction 4 | 95 | 6.70 | 28.58 | 0 | 36.11 | 45.08 | 81.19 | 4.86 | 13.73 | 0.22 |
| Fraction 5 | 96 | 6.77 | 35.36 | 0 | 12.61 | 82.81 | 95.42 | 1.26 | 3.25 | 0.07 |
| Fraction 6 | 52 | 3.67 | 39.03 | 0 | 9.2 | 87.42 | 96.62 | 0.92 | 2.38 | 0.08 |
| Fraction 7 | 109 | 7.69 | 46.72 | 0 | 2 | 97.18 | 99.18 | 0.22 | 0.59 | 0.01 |
| Fraction 8 | 97 | 6.85 | 53.56 | 0 | 0.57 | 99.07 | 99.64 | 0.13 | 0.21 | 0.02 |
| Fraction 9 | 114 | 8.05 | 61.61 | 0 | 0.18 | 99.68 | 99.86 | 0.00 | 0.12 | 0.02 |
| Fraction 10 | 110 | 7.76 | 69.37 | 0 | 0.01 | 99.95 | 99.96 | 0.00 | 0.02 | 0.02 |
| Fraction 11 | 92 | 6.49 | 75.86 | 0 | 0 | 99.97 | 99.97 | 0.00 | 0.01 | 0.02 |
| Fraction 12 | 121 | 8.54 | 84.40 | 0 | 0.01 | 99.95 | 99.96 | 0.00 | 0.01 | 0.03 |
| Fraction 13 | 95 | 6.70 | 91.11 | 0 | 0 | 99.97 | 99.97 | 0.00 | 0.00 | 0.03 |
| Bottom | 119 | 8.40 | 99.51 | 0 | 0 | 98.06 | 98.06 | 0.16 | 0.01 | 1.77 |
| Total | 1410.0 | | | | | | | | | |
| Loss | 7.0 | | | | | | | | | |
| Recovery | 99.50% | | | | | | | | | |

Olfactory assessment of the highly isomerically enriched components:

High-cis-pyranol acetate (>99% cis-(2-isobutyl-4-methyltetrahydropyran-4-yl) acetate of the formula (I.1)): iris-like note, a strong, clear bergamot-like note, a linalyl acetate-like note, a woody note, and a pepper/nutmeg-like note.

High-trans-pyranol acetate (>98% trans-(2-isobutyl-4-methyltetrahydropyran-4-yl) acetate of the formula (I.2)): jasmine-like note, a leather-like note and a strong fruit-like note.

In comparison with this, a mixture of 75% cis-(2-isobutyl-4-methyltetrahydropyran-4-yl) acetate (I.1) and 25% trans-(2-isobutyl-4-methyltetrahydropyran-4-yl) acetate (I.2) has the following olfactory properties: flowery, linalyl acetate, citrus. In view of this, both the olfactory properties of the high-cis-pyranol acetate and of the high-trans-pyranol acetate are surprising.

The invention claimed is:

1. A process for the preparation of isomerically pure cis-(2-isobutyl-4-methyltetrahydropyran-4-yl) acetate of the formula (I.1) or of isomerically pure trans -(2-isobutyl-4-methyltetrahydropyran-4-yl) acetate of the formula (I.2) or of an isomer mixture of (I.1) and (I.2), where the weight fraction of (I.1) or the weight fraction of (I.2) in the isomer mixture, based on the total weight of (I.1) and (I.2), is in a range from 90% by weight to less than 100% by weight, comprising:
   i) reacting an isomer mixture of cis-2-(2-methylpropyl)-4-hydroxy-4-methyltetrahydropyran (II.1) and trans-2-(2-methylpropyl)-4-hydroxy-4-methyltetrahydropyran (II.2)

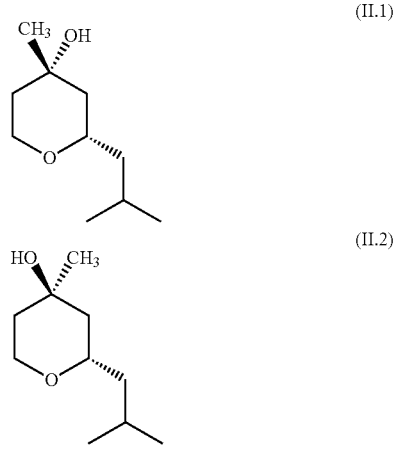

with a compound of the formula CH₃C(=O)-X, in which X is Cl, Br or CH₃C(=O)O,
   ii) optionally subjecting the reaction mixture obtained in step i) to a separation to give at least one fraction which comprises isomerically pure (I.1) or isomerically pure (I.2) or an isomer mixture of (I.1) and (I.2), where the weight fraction of (I.1) or the weight fraction of (I.2) in the isomer mixture, based on the total weight of (I.1) and (1.2), is in a range from 90% by weight to less than 100% by weight.

2. An isomerically pure cis-(2-isobutyl-4-methyltetrahydropyran-4-yl) acetate of the formula (I.1) or an isomer mixture of cis-(2-isobutyl-4-methyltetrahydropyran-4-yl) acetate (I.1) and trans-(2-isobutyl-4methyltetrahydropyran-4-yl) acetate (I.2), in which the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight.

3. An isomerically pure trans-(2-isobutyl-4-methyltetrahydropyran-4-yl) acetate of the formula (I.2) or an isomer mixture of cis-(2-isobutyl-4-methyltetrahydropyran-4-yl) acetate (I.1) and trans-(2-isobutyl-4-methyltetrahydropyran-4-yl) acetate (I.2), in which the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight.

4. A fragrance or aroma substance composition, comprising
   a) isomerically pure cis-(2-isobutyl-4-methyltetrahydropyran-4-yl) acetate of the formula (I.1) or isomerically pure trans-(2-isobutyl-4-methyltetrahydropyran-4-yl) acetate of the formula (I.2) or an isomer mixture of cis-(2-isobutyl-4-methyltetrahydropyran-4-yl) acetate (I.1) and trans-(2-isobutyl-4-methyltetrahydropyran-4-yl) acetate (I.2), where the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight, or the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight,
   b) optionally at least one further aroma chemical different from the compounds (I.1) and (I.2), and
   c) optionally at least one diluent,
with the proviso that the composition comprises at least one component b) or c).

5. The composition according to claim 4, comprising the component a) in a weight fraction of from 1 to 50% by weight, based on the total weight of the composition.

6. The composition according to claim 4, comprising the component a) in a weight fraction of from 0.1 to 70% by weight, based on the total weight of the composition.

7. A method for imparting and/or intensifying an odor or taste of a product with an iris-like note, a bergamot-like note, a linalyl acetate-like note, a woody note or a pepper/nutmeg-like note, comprising bringing the product into contact with an organoleptically effective amount of an isomerically pure cis-(2-isobutyl-4-methyltetrahydropyran-4-yl) acetate of the formula (I.1) or an isomer mixture, where the weight fraction of cis-(2-isobutyl-4-methyltetrahydropyran-4-yl) acetate (I. 1), based on the total weight of cis-(2-isobutyl-4-methyltetrahydropyran-4-yl) acetate (I.1) and trans-(2-isobutyl-4-methyltetrahydropyran-4-yl) acetate (L2), is in a range from 90% by weight to less than 100% by weight.

8. A method for imparting and/or intensifying an odor or taste of a product with a jasmine-like note, a leather-like note or a strong fruit-like note, in which the product is brought into contact with an organoleptically effective amount of an isomerically pure trans-(2-isobutyl-4-methyltetrahydropyran-4-yl) acetate of the formula (I.2) or an isomer mixture, where the weight fraction of trans-(2-isobutyl-4-methyltetrahydropyran-4-yl) acetate (I.2), based on the total weight of cis-(2-isobutyl-4-methyltetrahydropyran-4-yl) acetate (I.1) and trans-(2-isobutyl-4-methyltetrahydropyran-4-yl) acetate (I.2) is in a range from 90% by weight to less than 100% by weight.

9. A perfumed or aromatized product, comprising an organoleptically effective amount of isomerically pure cis-(2-isobutyl-4-methyltetrahydropyran-4-yl) acetate of the formula (I.1) or of isormerically pure trans-(2-isobutyl-4-methyltetrahydropyran-4-yl) acetate of the formula (I.2) or of an isomer mixture of cis-(2-isobutyl-4-methyltetrahydropyran-4-yl) acetate (I.1) and trans-(2-isobutyl-4-methyltetrahydropyran-4-yl) acetate (I.2), comprising an organoleptically effective amount of a fragrance or aroma substance composition as defined in claim 4.

10. The product according to claim 9, selected from the group consisting of scent dispensers and fragrances perfumes, detergents and cleaners, cosmetic compositions, bodycare compositions, hygiene articles, products for oral and dental hygiene, scent dispensers, fragrances, pharmaceutical compositions and crop protection compositions.

11. The use of isomerically pure cis-(2-isobutyl-4-methyltetrahydropyran-4-yl) acetate of the formula (I.1) or of an isomer mixture, where the weight fraction of cis-(2-isobutyl-4-methyltetrahydropyran-4-yl) acetate (I.1), based on the total weight of cis-(2-isobutyl-4-methyltetrahydropyran-4-yl) acetate (I.1) and trans-(2-isobutyl-4-methyltetrahydropyran-4-yl) acetate (I.2), is in a range from 90% by weight to less than 100% by weight, for the partial or complete replacement of linalyl acetate in a fragrance or aroma substance composition comprising linalyl acetate or in a product aromatized or perfumed with linalyl acetate.

* * * * *